US008303477B2

(12) United States Patent
Martin

(10) Patent No.: US 8,303,477 B2
(45) Date of Patent: Nov. 6, 2012

(54) FLUID RADIATION SHIELD FOR BRACHYTHERAPY

(75) Inventor: Gregory T. Martin, Somerville, MA (US)

(73) Assignee: Cytyc Corporation, Marlborough, MA (US)

( * ) Notice: Subject to any disclaimer, the term of this patent is extended or adjusted under 35 U.S.C. 154(b) by 1294 days.

(21) Appl. No.: 11/895,559

(22) Filed: Aug. 24, 2007

(65) Prior Publication Data

US 2009/0054721 A1 Feb. 26, 2009

(51) Int. Cl.
*A61M 3/00* (2006.01)
(52) U.S. Cl. .......................................................... 600/4
(58) Field of Classification Search .................. 600/1–8; 128/897, 898
See application file for complete search history.

(56) References Cited

U.S. PATENT DOCUMENTS

| | | | |
|---|---|---|---|
| 4,706,652 A | 11/1987 | Horowitz | |
| 4,754,745 A | 7/1988 | Horowitz | |
| 5,422,926 A | 6/1995 | Smith et al. | |
| 5,429,582 A | 7/1995 | Williams | |
| 5,484,384 A | 1/1996 | Fearnot | |
| 5,562,594 A | 10/1996 | Weeks | |
| 5,616,114 A * | 4/1997 | Thornton et al. | 600/3 |
| 5,724,400 A | 3/1998 | Swerdloff et al. | |
| 5,782,742 A | 7/1998 | Crocker et al. | |
| 5,800,333 A | 9/1998 | Liprie | |
| 5,803,895 A | 9/1998 | Kronholz et al. | |
| 5,851,182 A | 12/1998 | Sahadevan | |
| 5,863,284 A | 1/1999 | Klein | |
| 5,913,813 A * | 6/1999 | Williams et al. | 600/3 |
| 6,036,631 A | 3/2000 | McGrath et al. | |
| 6,482,142 B1 * | 11/2002 | Winkler et al. | 600/3 |
| 2005/0085681 A1 * | 4/2005 | Stubbs et al. | 600/3 |
| 2008/0177127 A1 | 7/2008 | Allan et al. | |

FOREIGN PATENT DOCUMENTS

| | | |
|---|---|---|
| EP | 0 867 200 | 9/1998 |
| WO | 97/19723 | 6/1997 |
| WO | WO98/25674 | 6/1998 |
| WO | WO99/11325 | 3/1999 |
| WO | WO99/33515 | 7/1999 |
| WO | WO99/42163 | 8/1999 |

OTHER PUBLICATIONS

Kassas et al., Contrast Effects on Dosimetry of a Partial Breast Irradiation System, American Association of Physicists in Medicine, 1976-9, vol. 31 / No. 7, Univ. of Texas MD Anderson Cancer Center, Houston (Jul. 2004).
Testolin et al., Dual-energy X-ray Absorptiometry: Analysis of Pediatric Fat Estimate Errors Due to Tissue Hydration Effects, J Appl Physiol., 2365-72, vol. 89 / No. 6, Department of Pediatrics, San Raffaele Hospital, Milano, Italy (Dec. 2000).

(Continued)

*Primary Examiner* — Samuel Gilbert

(57) ABSTRACT

A brachytherapy treatment device includes an insertion member, an expandable chamber, and first and second immiscible fluids. The insertion member has proximal and distal ends. The expandable chamber is disposed on the distal end of the insertion member and has an inner surface defining a three-dimensional volume. First and second immiscible fluids are disposed within the expandable chamber and have different radiation absorption properties. At least one of the first and second immiscible fluids forms a fluid radiation shield having a predetermined orientation within the three-dimensional volume. First and second immiscible fluids may have different densities and utilize fluid buoyancy to form an symmetric fluid radiation shield to create an asymmetric radiation dosing profile relative to an inner boundary of a treatment site. Methods for performing brachytherapy treatment include positioning fluids and/or a patient to form an asymmetric fluid radiation shield in a desired orientation to protect sensitive tissues.

17 Claims, 7 Drawing Sheets

OTHER PUBLICATIONS

Cheng et al., Dose Perturbations due to Contrast Medium and Air in MammoSite® Treatment: An Experimental and Monte Carlo Study, American Association of Physicists in Medicine, 2279-87, vol. 32 / No. 7, Arizona Oncology Associates, Tucson (Jul. 2005).

X. Allen Li, Dosimetric Effects of Contrast Media for Catheter-based Intravascular Brachytherapy, American Association of Physicists in Medicine, 757-63, vol. 28 / No. 5, Department of Radiation Oncology, University of Maryland, Baltimore (May 2001).

de Dreuille et al., Bone Equivalent Liquid Solution to Assess Accuracy of Transmission Measurements in SPECT and PET, IEEE Transactions on Nuclear Science, 1186-90, vol. 44 / No. 3, Service Hospitalier Frederic Joliot, Orsay, France (Jun. 1997).

Watkin et al., Multi-Modal Contrast Agents: A First Step, Academic Radiology, S285-89, vol. 9 / Suppl. 2, Medical Ultrasound Research Laboratory, University of Illinois, Urbana (2002).

B. H. Hasegawa, Chapter 4: Physical Determinants of Contrast, "The Physics of Medical X-Ray Imaging", 2nd Ed., 1-23, Medical Physics Pub. (1991).

Ye et al., Dose Errors due to Inhomogeneities in Balloon Catheter Brachytherapy for Breast Cancer, Int J Radiat Oncol Biol Phys., 672-7, vol. 60 / No. 2, Department of Radiation Oncology, University of Alabama School of Medicine, Birmingham (Oct. 2004).

\* cited by examiner

FLUID RADIATION SHIELD FOR BRACHYTHERAPY

TECHNICAL FIELD

This technology relates generally to brachytherapy devices and methods for use in treating proliferative tissue disorders.

BACKGROUND

Body tissues subject to proliferative tissue disorders, such as malignant tumors, are often treated by surgical resection of the tumor to remove as much of the tumor as possible. Unfortunately, the infiltration of the tumor cells into normal tissues surrounding the tumor may limit the therapeutic value of surgical resection because the infiltration can be difficult or impossible to treat surgically. Radiation therapy may be used to supplement surgical resection by targeting the residual tumor margin after resection, with the goal of reducing its size or stabilizing it. Radiation therapy may be administered through one of several methods, or a combination of methods, such as interstitial or intercavity brachytherapy. Brachytherapy may also be administered via electronic brachytherapy using electronic sources, such as x-ray sources, for example.

Brachytherapy is radiation therapy in which the source of radiation is placed in or close to the area to be treated, such as within a cavity or void left after surgical resection of a tumor. Brachytherapy may be administered by implanting or delivering a spatially confined radioactive material to a treatment site, which may be a cavity left after surgical resection of a tumor. For example, brachytherapy may be performed by using an implantable device (e.g., catheter or applicator) to implant or deliver radiation sources directly into the tissue(s) or cavity to be treated. During brachytherapy treatment, a catheter may be inserted into the body at or near the treatment site and subsequently a radiation source may be inserted through the catheter and placed at the treatment site.

Brachytherapy is typically most appropriate where: 1) malignant tumor regrowth occurs locally, within 2 or 3 cm of the original boundary of the primary tumor site; 2) radiation therapy is a proven treatment for controlling the growth of the malignant tumor; and 3) there is a radiation dose-response relationship for the malignant tumor, but the dose that can be given safely with conventional external beam radiotherapy is limited by the tolerance of normal tissue. Interstitial and/or intercavity brachytherapy may be useful for treating malignant brain and breast tumors, among other types of proliferative tissue disorders.

There are two basic types of brachytherapy, high dose rate and low dose rate. These types of brachytherapy generally include the implantation of radioactive "seeds," such as palladium or iodine, into the tumor, organ tissues, or cavity to be treated. Low dose rate (LDR) brachytherapy refers to placement of multiple sources (similar to seeds) in applicators or catheters, which are themselves implanted in a patient's body. These sources are left in place continuously over a treatment period of several days, after which both the sources and applicators are removed. High dose rate brachytherapy (HDR) uses catheters or applicators similar to those used for LDR. Typically, only a single radiation source is used, but of very high strength. This single source is remotely positioned within the applicators at one or more positions, for treatment times which are measured in seconds to minutes. The treatment is divided into multiple sessions ('fractions'), which are repeated over a course of a few days. In particular, an applicator (also referred to as an applicator catheter or treatment catheter) is inserted at the treatment site so that the distal region is located at the treatment site while the proximal end of the applicator protrudes outside the body. The proximal end is connected to a transfer tube, which in turn is connected to an afterloader to create a closed transfer pathway for the radiation source to traverse. Once the closed pathway is complete, the afterloader directs its radioactive source (which is attached to the end of a wire controlled by the afterloader) through the transfer tube into the treatment applicator for a set amount of time. When the treatment is completed, the radiation source is retracted back into the afterloader, and the transfer tube is disconnected from the applicator.

A typical applicator catheter comprises a tubular member having a distal portion which is adapted to be inserted into the patient's body, and a proximal portion which extends outside of the patient. A balloon is provided on the distal portion of the tubular member which, when placed at the treatment site and inflated, causes the surrounding tissue to substantially conform to the surface of the balloon. In use, the applicator catheter is inserted into the patient's body, for instance, at the location of a surgical resection to remove a tumor. The distal portion of the tubular member and the balloon are placed at, or near, the treatment site, e.g. the resected space. The balloon is inflated, and a radiation source is placed through the tubular member to the location within the balloon.

Several brachytherapy devices are described in U.S. Provisional Patent Application 60/870,690, entitled "Brachytherapy Device and Method," and U.S. Provisional Patent Application 60/870,670, entitled "Asymmetric Radiation Dosing for Devices and Methods," both filed on Dec. 19, 2006, which are both commonly owned with the present application; U.S. Pat. No. 5,913,813; and U.S. Pat. No. 6,482,142; each of which is hereby incorporated by reference herein in their entireties.

The dose rate at a target point exterior to a radiation source is inversely proportional to the square of the distance between the radiation source and the target point. Thus, previously described applicators, such as those described in U.S. Pat. No. 6,482,142, issued on Nov. 19, 2002, to Winkler et al., are symmetrically disposed about the axis of the tubular member so that they position the tissue surrounding the balloon at a uniform or symmetric distance from the axis of the tubular member. In this way, the radiation dose profile from a radiation source placed within the tubular member at the location of the balloon is symmetrically shaped relative to the balloon. In general, the amount of radiation desired by a treating physician is a certain minimum amount that is delivered to a region up to about two centimeters away from the wall of the excised tumor, i.e. the target treatment region. It is desirable to keep the radiation that is delivered to the tissue in this target tissue within a narrow absorbed dose range to prevent overexposure to tissue at or near the balloon wall, while still delivering the minimum prescribed dose at the maximum prescribed distance from the balloon wall (i.e. the two centimeter thickness surrounding the wall of the excised tumor).

However, in some situations, such as a treatment site located near sensitive tissue like a patient's skin, the symmetric dosing profile may provide too much radiation to the sensitive tissue such that the tissue suffers damage or even necrosis. In such situations, the dosing profile may cause unnecessary radiation exposure to healthy tissue or it may damage sensitive tissue, or it may not even be possible to perform a conventional brachytherapy procedure.

To alleviate some of these problems associated with prior applicators, U.S. Pat. No. 6,482,142, discloses several approaches to creating an asymmetric dosing profile relative to the balloon profile. In one approach, an asymmetric dosing profile is produced by shaping or locating the radiation source so as to be asymmetrically placed with respect to the longitudinal axis of the balloon. In an alternative approach, the applicator is provided with asymmetric radiation shielding located between the radiation source and the target tissue.

However, the devices and methods disclosed in U.S. Pat. No. 6,482,142 have several drawbacks. For one, asymmetrically placing the radiation source decreases the radiation dosing profile in certain directions, but correspondingly increases the radiation dosing profile in the other directions. The devices also do not allow for adjustment of the amount of asymmetry and/or the resulting radiation dosing profile shape. In addition, the shielded devices are permanently affixed to the applicator such that they can interfere with pre-radiation treatment procedures such as imaging or other low energy procedures.

Accordingly, there remains a need for additional methods and devices which can provide an asymmetric radiation dosing profile having a predetermined orientation during brachytherapy procedures.

SUMMARY

Brachytherapy treatment devices and methods are disclosed herein. In one embodiment, a brachytherapy treatment device has an insertion member, an expandable chamber, and first and second immiscible fluids. The insertion member has a proximal end and a distal end. The expandable chamber is disposed on the distal end of the insertion member and has an inner surface defining a three-dimensional volume. The first and second immiscible fluids are disposed within the expandable chamber and have different radiation absorption properties. At least one of the first and second immiscible fluids forms a fluid radiation shield having a predetermined orientation within the three-dimensional volume.

In one embodiment, a brachytherapy treatment device comprises a tubular insertion member and an expandable chamber. The tubular insertion member has a proximal end and a distal end. The expandable chamber is disposed on the distal end of the tubular insertion member and has an inner surface defining a three-dimensional volume. The expandable chamber is adapted to receive first and second immiscible fluids having different radiation absorption properties. The first and second immiscible fluids form a fluid radiation shield having a predetermined orientation within the three-dimensional volume. The tubular insertion member may further comprise at least first and second lumens fluidly connecting the proximal and distal ends, each of the first and second lumens adapted to receive first and second immiscible fluids respectively.

In another embodiment, a method for performing brachytherapy treatment is disclosed. The method includes: placing a catheter within a patient at a treatment site, wherein the catheter has a proximal end, a distal end, and an expandable chamber disposed thereon, the expandable chamber inflatable to substantially fill the inner boundary of the treatment site; injecting at least first and second immiscible fluids into the expandable chamber, wherein the first and second immiscible fluids have different radiation absorption properties; and placing a radiation source at the treatment site, wherein orientation of the first and second immiscible fluids relative to the radiation source forms a predetermined fluid radiation shield.

In yet another embodiment a brachytherapy treatment kit includes a catheter and first and second immiscible fluids having different radiation absorption properties. The catheter has proximal and distal ends and an expandable chamber disposed on the distal end. At least the first and second immiscible fluids are disposed within the expandable chamber and form a fluid radiation shield having a predetermined orientation relative to an inner boundary of a treatment site.

The brachytherapy treatment devices and methods disclosed herein may be oriented to provide an asymmetric fluid radiation shield to create an asymmetric radiation dosing profile relative to an inner boundary of target tissue at a treatment site. In some implementations, the first and second immiscible fluids may have different densities and may utilize fluid buoyancy to orient within the expandable chamber. The fluid radiation shields function to protect tissues from receiving an undesirably high dose of radiation while still allowing the remainder of target tissue at a treatment site to receive a prescribed therapeutic dosage of radiation treatment. Because the shield is a fluid shield formed within the expandable chamber, it can be easily formed and removed (by injecting and removing fluids) so that it does not interfere with pre-radiation treatment imaging or other procedures.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1:
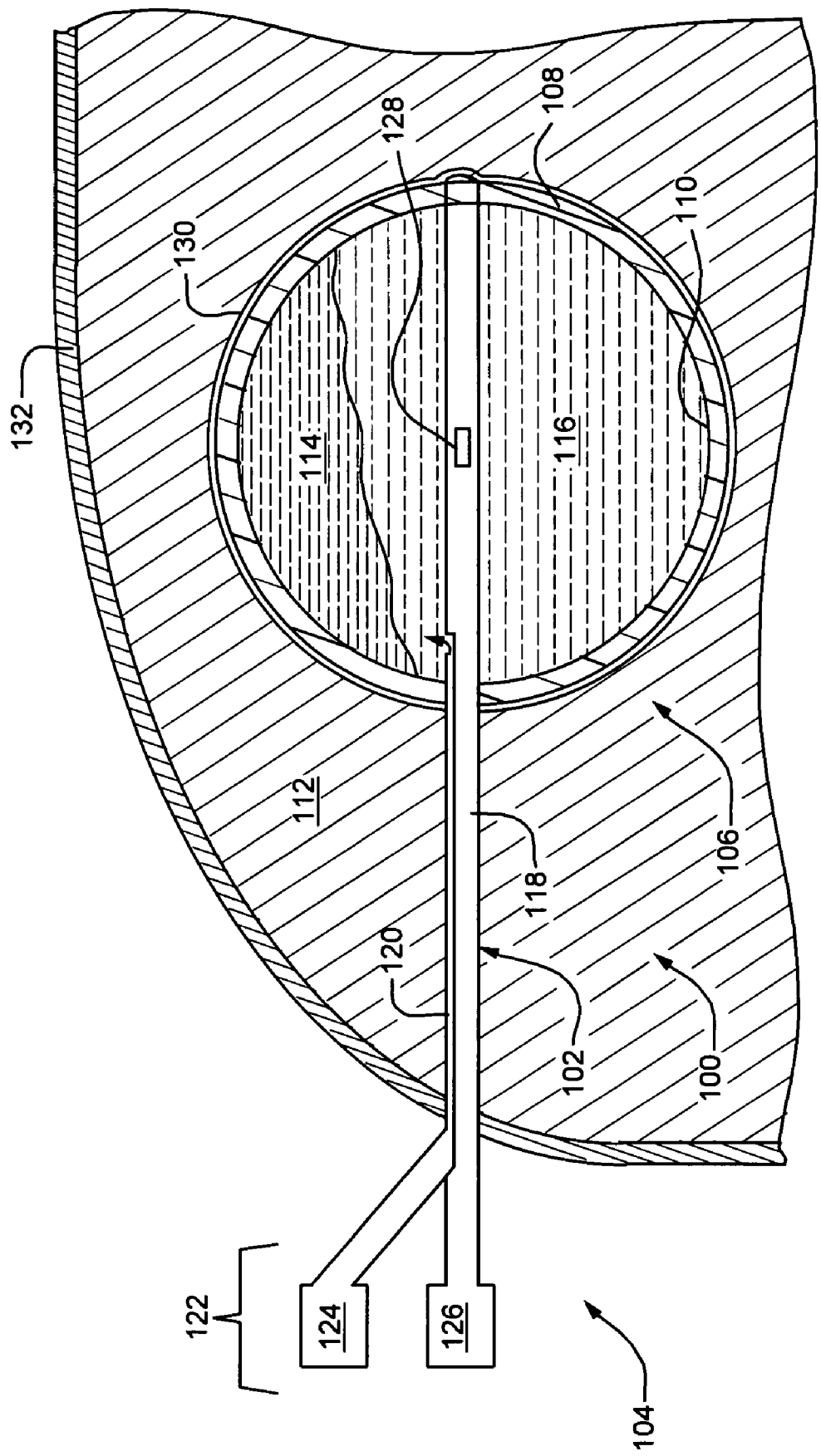
FIG. 1 illustrates a cross-sectional view of an exemplary brachytherapy treatment device.

The brachytherapy treatment devices and methods disclosed herein provide a fluid radiation shield which may be oriented in any number of configurations to protect sensitive tissues while still allowing target tissues to receive an appropriate therapeutic dose of radiation. The brachytherapy treatment devices and methods disclosed herein may be administered using radioactive sources or using electronic sources, such as x-ray technology, when providing electronic brachytherapy treatment. Referring now to the drawing figures, like numerals indicate like features throughout the drawing figures shown and described herein.

With reference to FIG. 1, a brachytherapy applicator or treatment device 100 (also commonly referred to as an applicator catheter or treatment catheter) may comprise an elongated tubular insertion member 102 having a proximal end 104 and a distal end 106. The distal end 106 is adapted to be inserted into a patient's body and the proximal end is adapted to extend outside of the patient's body.

The insertion member 102 may be formed of a flexible material, including without limitation various plastic or elastomeric polymers and/or other suitable materials. The insertion member 102 should be flexible and soft enough that it conforms to surrounding tissue 112 and easily bends when force is applied, such as by movement of the patient's body (shown in part as tissue 112), making the insertion member 102 more comfortable. The insertion member 102 may further comprise a malleable element adapted to confer a shape upon at least a portion of its length. The walls of the insertion member 102 may be substantially impermeable to fluids, except where there are apertures and/or openings disposed within the walls of the tubular insertion member 102.

The device 100 may further comprise an expandable chamber 108 disposed on the distal end 106 of the insertion member 102 and having an inner surface 110 defining a three-dimensional volume. The volume defined by the expandable chamber 108, when inflated, should be substantially similar to the volume of the cavity 130 to substantially fill the cavity 130 and help provide a substantially uniform and symmetrical boundary. The expandable chamber 108 may be any device which can be controllably expanded and contracted to retract surrounding tissue 112, such as a balloon or other device.

The expandable chamber 108 may be formed of a variety of different materials, such as biocompatible polymers. Some exemplary biocompatible polymers may include silastic rubbers, polyurethanes, polyethylene, polypropylene, and polyester, just to name a few examples. The walls of the expandable chamber 108 will be formed of a radiation transparent material to allow radiation to pass through the walls of the expandable chamber 108 to treat the tissue of the cavity 130 surrounding the expandable chamber 108. In some embodiments, it may be desirable to use one or more expandable chambers 108, 109 (shown in FIG. 2) or double-walled chambers to minimize the risk of fluid leakage from the expandable chamber into a patient, such as may occur if one chamber becomes punctured.

As shown in FIG. 1, first and second immiscible fluids 114, 116 may be disposed within the expandable chamber 108. The first and second immiscible fluids 114, 116 may generally comprise one or a combination of injection fluids, inflation fluids, and radiation shielding fluids. The first and second immiscible fluids 114, 116 may comprise radiation absorbing or attenuating materials or contrast materials and may take the form of a fluid, liquid, gas, slurry, gel, solid, or semi-solid. In one embodiment, the first and second immiscible fluids 114, 116 have different radiation absorption properties and may be independently positionable within the expandable chamber 108. At least one of the first and second immiscible fluids 114, 116 may be positioned to form a fluid radiation shield (shown as first immiscible fluid 114 in FIG. 1) having a predetermined orientation within the three-dimensional volume.

As shown in FIG. 1, the elongated tubular insertion member 102 may also include a main lumen 118 extending between and operably coupling the proximal 104 and distal 106 ends of the insertion member 102. The main lumen 118 may be a radiation source pathway configured to receive a radiation source and provide a pathway for positioning a radiation source at radiation source position 128 within the expandable chamber 108. In alternative embodiments, there may be multiple source lumens configured to receive a radiation source and provide pathways for positioning a radiation source at similar or different positions within the expandable chamber 108. The main lumen 118 of the insertion member 102 may further comprise a plurality of other tubes or lumens disposed therein to provide several separate and independently operable pathways for accessing the distal end 106 of the insertion member 102 via the proximal end 104 of the insertion member 102.

Figure 2:
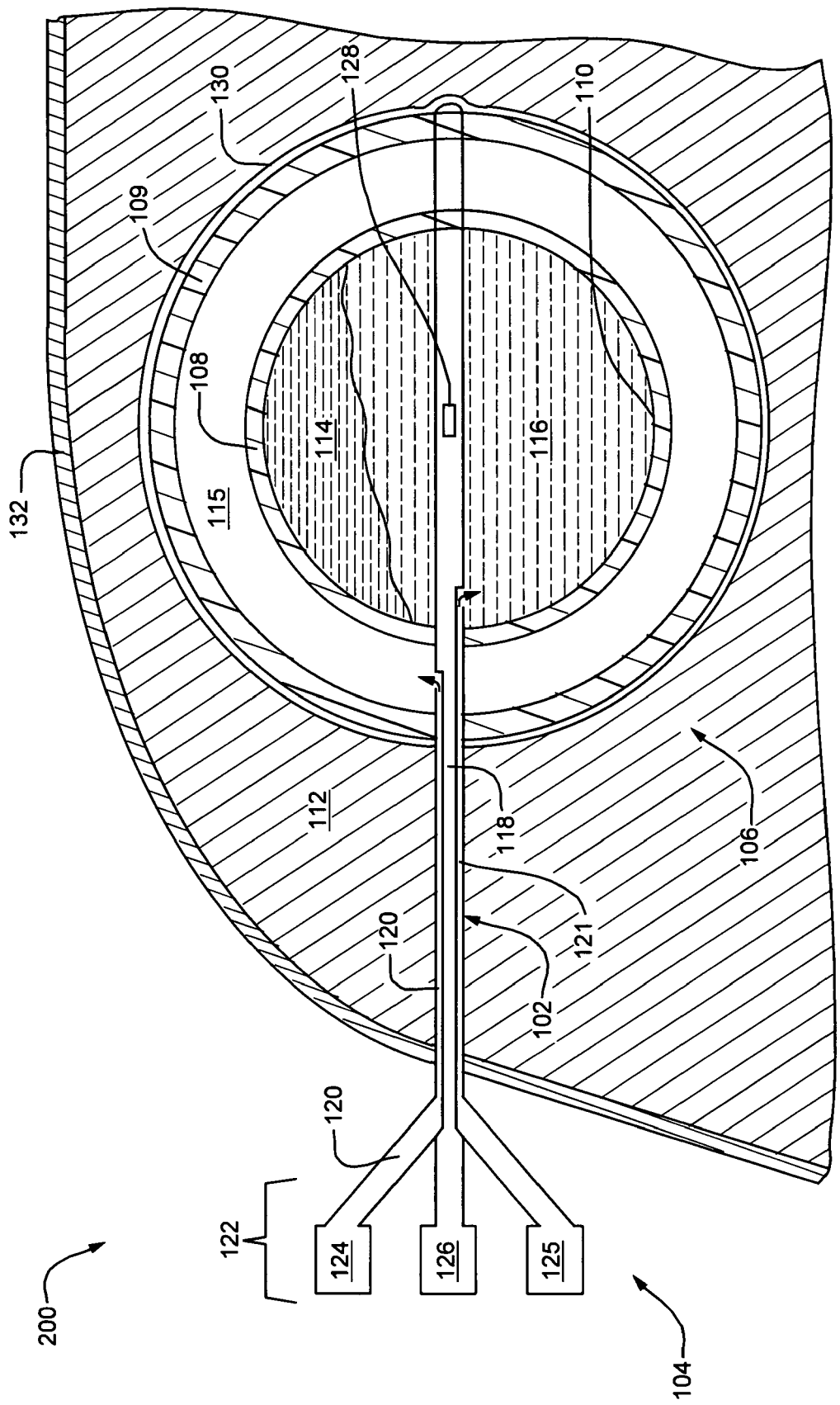
FIG. 2 illustrates a cross-sectional view of an exemplary brachytherapy treatment device having a plurality of expandable chambers.

The main lumen may further comprise an inflation lumen 120, such as a balloon inflation tube 120, disposed within the main lumen 118 and fluidly coupling the expandable chamber 108 and the proximal end 104 of the insertion member 102. The inflation lumen 120 provides a fluid pathway, allowing the expandable chamber 108 to be remotely expanded/inflated and contracted/deflated from a location at the proximal end 104 of the insertion member 102, such as by a user or machine. In some embodiments, the main lumen 118 may comprise multiple inflation lumens 120, 121 for inflating multiple expandable chambers 108, 109 (as shown in FIG. 2) pathways. In yet additional embodiments, the main lumen 118 and/or other inflation lumens 120, 121 may comprise curved or articulating portions at the distal end 106 within expandable chamber 108. Curving, bending or articulating of the lumens may provide multiple alternative radiation source positions within the expandable chamber, thus providing multiple options for orientation of the isodose profile and for treatment planning.

Figure 3:
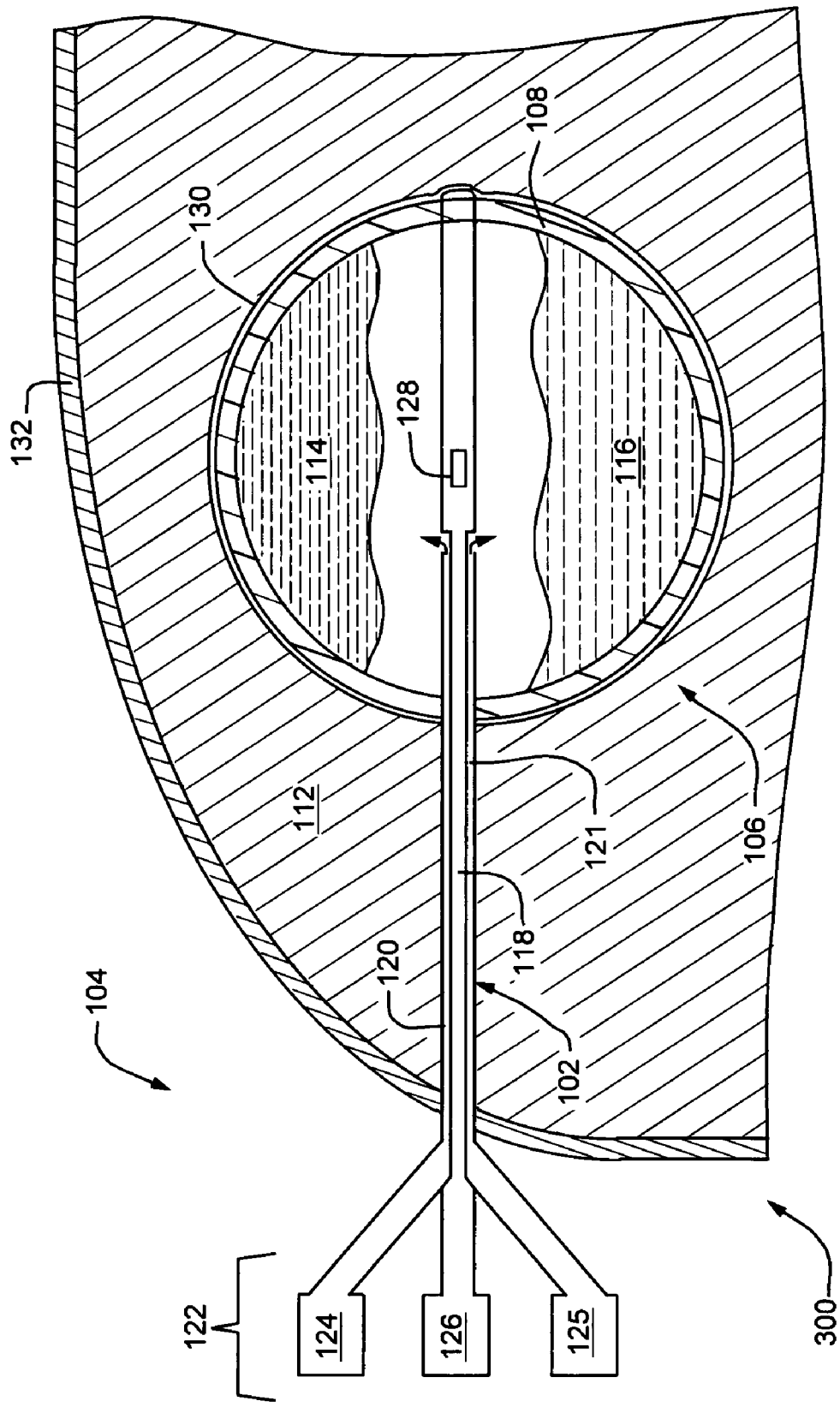
FIG. 3 illustrates a tubular insertion member having first and second lumens fluid connecting the proximal and distal ends.

An exemplary brachytherapy treatment device 100 may also have a hub 122 disposed on the proximal end 104 of the insertion member. The hub 122 may have one or a plurality of ports 124, 125, 126, operably coupled to main lumen 118 and/or inflation lumens 120, 121, as shown in FIGS. 2 & 3. The ports 124, 125, 126 may be formed of appropriate materials, such as plastic for example, and may be sealed to prevent leakage of fluids from the main lumen 118 and/or inflation lumens 120, 121.

In one exemplary implementation as shown in FIG. 1, a first port 126 is coupled to main lumen 118 may be adapted to receive a radiation source to allow the radiation source to be positioned within the expandable chamber 108 at a radiation source position 128. A second port 124 coupled to and in fluid communication with inflation lumen 120 may be used to inject and/or remove fluids 114, 116 from the expandable chamber 108. In an alternative embodiment, as shown in FIG. 2, a third port 125 may be coupled to and in fluid communication with inflation lumen 121 to inject and/or remove fluids from inner expandable chamber 108, while a second port 124 may be coupled to and in fluid communication with inflation lumen 120 to inject and/or remove fluids from the outer expandable chamber 109. Ports 124, 125, 126 First are described and shown generally herein only for purposes of illustration. Hub 122 may contain any number of ports having any number of configurations.

In one embodiment, shown in FIG. 2, multiple expandable chambers 108, 109 (i.e., balloons) may be used. In the embodiment shown in FIG. 2, the expandable chambers 108, 109 are positioned to surround one another to provide an additional level of safety in case one of the chambers is punctured during treatment. Additionally, the use of multiple expandable chambers allows for each chamber to contain multiple immiscible fluids, creating an unlimited number of fluid shielding configurations. Any number of expandable chambers may be used and these chambers may or may not be positioned to surround one another. In some implementations, the expandable chambers may also be mounted adjacent one another.

As shown in FIG. 2, a first expandable chamber 108 may have a smaller inflation diameter that than of outer expandable chamber 109. The first and second expandable chambers 108, 109 may have separate inflation lumens 118, 120 so that each expandable chamber can be independently inflated to fit a treatment site of any size or shape and to create a desired tissue configuration about the radiation source position 128. As shown in FIG. 2, the inner expandable chamber 108 may contain first and second immiscible fluids 114, 116, and outer expandable chamber 109 may contain a third immiscible fluid 115. It is also contemplated herein that outer expandable chamber 109 may contain first and second immiscible fluids 114, 116 and inner chamber 108 may contain a third 115 or multiple immiscible fluids. The utilization of multiple expandable chambers containing multiple immiscible fluids having varied radiation absorption properties creates an unlimited number of fluid shielding configurations, as will be known by those of skill in the art after having become familiar with the teachings herein.

In yet another embodiment 300 shown in FIG. 3, the tubular insertion member 102 may comprise at least first 120 and second 121 lumens fluidly connecting the proximal 104 and distal 106 ends of the insertion member 102. Each of the first and second lumens 120, 121 may be adapted to receive first and second immiscible fluids 114, 116 respectively. In this implementation, hub 122 may comprise three ports 124, 126, and 125 for receiving a first fluid 114, a radiation source (not shown), and a second fluid 116, respectively.

As shown in FIG. 3, the appropriate orientation of the first and second immiscible fluids 114, 116 may be facilitated by the ability to inject the fluids through separate inflation lumens 120, 121 having separate ports within the expandable chamber 108. The orientation of the ports within the expandable chamber 108 may help ensure appropriate fluid positioning within the expandable chamber 108. In this implementation, the first and second immiscible fluids 114, 116 may also be injected simultaneously to orient more rapidly within the expandable chamber 108. FIG. 3 illustrates the initial injection of first and second immiscible fluids 114, 116 and it is important to note that the expandable chamber 108 is not yet fully inflated in FIG. 3. It is also contemplated that the multiple fluid lumens could be utilized in combination with multiple expandable chambers.

The brachytherapy treatment devices disclosed herein provide fluid radiation shielding during brachytherapy treatment of a patient. To deliver the brachytherapy treatment to a treatment site within a patient, the radiation source (not shown) may be placed at the radiation source position 128 (e.g., treatment site 112) via the insertion member 102. Once placed at the treatment site 112, the radiation source creates a radiation dose distribution profile which takes the shape of spherical isodose shells that are centered on the location of the radiation source. When the radiation source within the expandable chamber 108 is positioned close to sensitive tissue, such as skin 132, it is possible that the sensitive tissue 132 may receive an undesirably high radiation dose.

The issue of protecting sensitive tissues 132, such as skin, is commonly referred to as skin spacing, and is an important consideration in treatment planning. Without any radiation shielding, it may be necessary to ensure sufficient tissue depth exists between sensitive tissues 132 and the cavity 130 to prevent damage to the sensitive tissues during treatment. Fluid radiation shielding may provide a means for treating areas where tissue depth is minimal between sensitive tissues 132 and the cavity 130. Additionally, the fluid radiation shield may be positioned in an unlimited number of orientations to provide a larger variety of treatment planning options for patients. Further, because the fluid radiation shield is removable, it does not interfere with pre-radiation treatment imaging or other procedures at the treatment site.

Figure 4:
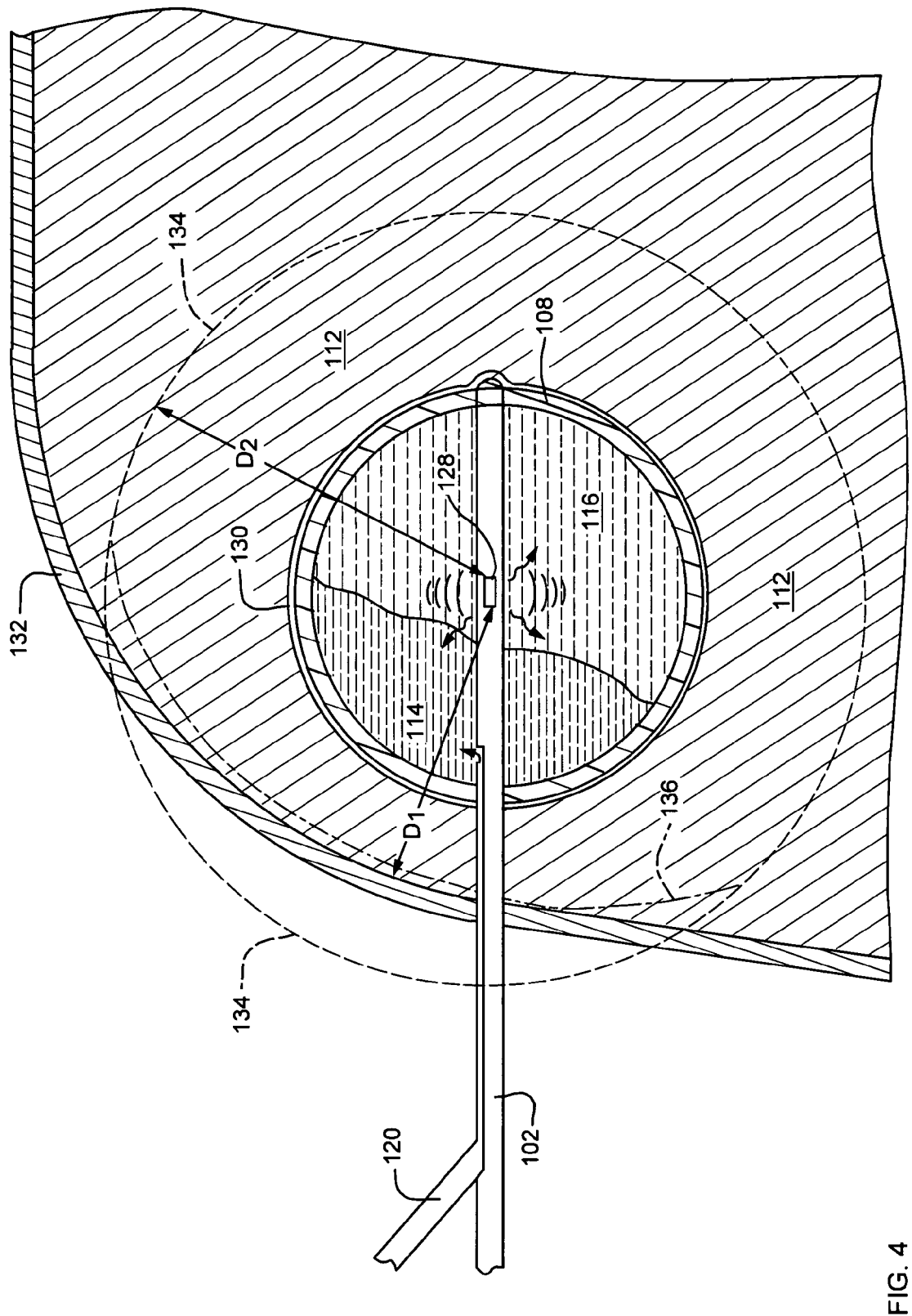
FIG. 4 illustrates an exemplary brachytherapy treatment device positioned at a treatment site and spacing distances between a radiation source position, target tissues, and sensitive tissues.

FIG. 4 generally illustrates spacing distances (D) between a radiation source position 128, sensitive tissues 132 (e.g., skin), and target treatment areas 112. The target treatment area 112 is illustrated generally as the approximately circular area surrounding the inner boundary or margin 130 of the resected tumor. A radiation source positioned at the radiation source position 128 will emit radiation to produce an isodose profile relative to the inner boundary 130 of target tissue 112 to be treated, without the effect of any radiation shielding. The radiation dose from a radiation source (positioned at radiation source position 128) is typically emitted substantially equally in all 360° surrounding the radiation source position (shown generally as radiation dose profile 134), assuming the radiation source has no abnormalities or shielding thereon. As shown in FIG. 4, sensitive tissue (e.g., skin 132) falls within the radiation does profile 134 and thus may receive an undesirably high dose of radiation, resulting in damage to the skin 132.

With continuing reference to FIG. 4, the distance ($D_1$) or spacing between the skin 132 and radiation source position 128 is substantially less than that of the distance ($D_2$) between the other surrounding target tissues 112 and that of the radiation source position 128. Because the radiation dose is emitted substantially equally in all directions, and because it decreases based upon the square of the distance, the proximity of the skin 132 to the radiation source 128 results in the skin 132 receiving an undesirably high and potentially very damaging dose of radiation. It is therefore advantageous to shield the skin 132 from receiving such a high dose of radiation while still allowing the remainder of the target tissue 112 to receive a prescribed therapeutic dosage of radiation treatment.

FIG. 4 also illustrates a desired orientation of a fluid radiation shield 114 with relation to skin 132, wherein the fluid radiation shield 114 creates an asymmetric radiation dosing profile (shown generally as 136) relative to the inner boundary of target tissue 130. The fluid radiation shield changes or alters the radiation dosing profile and this may be done to form an asymmetric radiation dosing profile or to form a symmetric radiation dosing profile. Regardless, the fluid radiation shield reshapes the radiation dosing profile to enable an appropriate dose of brachytherapy treatment to be delivered, even when the treatment site is very close to sensitive tissues, such as skin. The fluid radiation shield may also be used to direct, as well as reshape, the radiation dosing profile to minimize unnecessary exposure to healthy tissue. The asymmetric radiation dosing profile 136 is shown in FIG. 4 generally as dashed line 136, but may have a number of different configurations depending upon the particular shielding fluid used and the quantity, density, and/or radiation absorption properties of that fluid, as will be described in more detail below.

It is important to note that the fluid radiation shield may be composed of different materials or combinations of materials having different thickness in order to provide varying degrees of radiation absorption or attenuation. For example, thick or dense materials may be used to provide more attenuation, which can be localized or directed to produce a desired dosing pattern. Additionally, the shield may be formed of a composite of more than one material or thickness in order to provide varying degrees of attenuation. For example, the shield may be thicker in the direction of sensitive tissue in order to reduce or even block the radiation dose applied to the sensitive tissue and/or the shield may be thinner in the opposite direction in order to provide a higher radiation dose to the target tissue.

The immiscible fluids 114, 116 may generally comprise one or a combination of injection fluids, inflation fluids, and radiation shielding fluids. The first and second immiscible fluids 114, 116 having different radiation absorption or attenuation properties may have any measure of radiation absorption or attenuation properties. In some embodiments, first and second immiscible fluids 114, 116 may have minimal radiation absorption properties to allow a substantial amount of radiation through. In other embodiments, first and second immiscible fluids 114, 116 may have maximum radiation absorption properties to allow minimal or no radiation through. In some implementations, such as where density of the fluids could be changed, a type of physical state change may also affect radiation absorption or attenuation properties of the fluids 114, 116.

Immiscible fluids or liquids 114, 116 of different densities may also have a natural difference in their absorption of radiation energy, such as water and oil based liquids. For instance, liquid silicones, fluorosilicones, and perfluorocarbon liquids, such as those routinely used in retinal attachment surgery and other medical procedures, could be used as fluid(s) for the liquid radiation shield, while water or water-based solutions could be used as inflation fluid(s). These oil-based and water-based fluids have different densities allowing the oil-based fluids to separate from the water-based fluids via the action of buoyancy.

Radiation is attenuated as a function of the thickness of the fluid layer, the density of the fluid, and the effective atomic number (Z) of the molecules in the fluid. For example, pure water has a density of 1.0 g/cm$^3$, an effective atomic number (Z) of 7.5, and a linear coefficient of attenuation (at 100 keV photon energy) of 0.17 l/cm. Thus, for a 100 keV x-ray source, a 1 cm thickness of water will attenuate 17% (0.17) of the x-ray photons in the beam of radiation. In contrast, a material such as silicone, which has a higher atomic number (Z), would impart more radiation attenuation. Thus, a material such as silicone may be used as a radiation shielding fluid.

In other embodiments, the composition of the radiation shielding liquid may be modified to increase its attenuation of radiation. The liquid composition may be modified by mixing molecules that attenuate radiation into the shielding fluid. For instance, materials used as contrast agents for Xray imaging may be used for this purpose. These contrast agents typically contain iodine (Z=53), barium (Z=56), or some other element with an atomic number (Z) higher than water. Thus, when such contrast agents are mixed into a shielding fluid(s), the radiation may be preferentially attenuated.

In another embodiment, the inflation fluid may also comprise a fluid that contains a radiation source, such as Iotrex® or other solutions that use Iodine-125 or Iodine-131, such as those used during low dose radiotherapy. A fluid(s) containing a slurry of radioactive material(s) may also be used. Additionally, the radioactive material may be encapsulated within a gel.

The number of immiscible fluids 114, 116 used, the type of immiscible fluid used, the quantities of each type of fluid to be used, as well as the specific radiation absorption and/or attenuation properties of each of the immiscible fluids may be varied to specifically tailor the fluid radiation shielding to each treatment site size and orientation, as will be know by those of ordinary skill in the art after having become familiar with the teachings herein. The examples shown herein are exemplary for purposes of illustration only, and should not be considered to be limiting.

The first and second immiscible fluids 114, 116 may be disposed within the expandable chamber 108 in a number of different forms, such as in fluid, gas, liquid, gel, slurry, or semi-solid form. In some implementations, the first and second immiscible fluids 114, 116 may comprise a slurry of solid particles suspended in a liquid medium for delivery. The first and second immiscible fluids 114, 116 may be disposed within the expandable chamber in any order and may be injected simultaneously or at different times. Additionally, the first and second immiscible fluids 114, 116 (or plurality of fluids) may be combined or injected separately.

In some embodiments, first and second immiscible fluids 114, 116 may be disposed within the expandable chamber 108 in a first physical state and may then be stimulated or activated while in the expandable chamber 108 to induce a change to a different physical state. In some embodiments, the first and second immiscible fluids 114, 116 may undergo more than one physical state change while in the expandable chamber 108. For example, in one implementation, at least one of the first and second immiscible fluids 114, 116 may be disposed or injected into the expandable chamber 108 in one physical state, and may be changed to another physical state for treatment, and may then be changed to another physical state for removal from the expandable chamber 108. In this embodiment, at least one of the first and second immiscible fluids 114, 116 may be injected in a liquid form and may then be exposed to a stimuli to induce a change into a semi-solid, gel, or solid material to freeze it into place during treatment. Once treatment is concluded, the semi-solid, gel, or solid material may be exposed to a stimuli to induce another change into a liquid state for easier removal via an inflation lumen 120, 121.

In yet additional implementations, first and second immiscible fluids 114, 116 may even be disposed as particles in a solid or semi-solid state which may then be dissolved and/or undergo a physical state change. In another implementation, there may be a time delay between injecting the first and second immiscible fluids. For example, a first immiscible fluid may be injected into the expandable chamber 108 before the second immiscible fluid is injected. In another example, a first immiscible fluid may be injected and then exposed to stimuli to induce a type of physical state change to freeze or gel the fluid into place, before injecting a second immiscible fluid.

The first and second immiscible fluids 114, 116 may be positioned or oriented within the three-dimensional volume in the expandable chamber 108 using a variety of different techniques. In one embodiment, the first and second immiscible fluids 114, 116 may each have different radiation absorption properties and different densities. When the first and second immiscible fluids 114, 116 have different densities, they may be oriented using gravity and fluid buoyancy to position them. For example, a fluid with a lower density with rise above or "float" on top of a fluid having a higher density, thus allowing fluids with different densities to be oriented with relation to the direction of gravity (i.e., utilizing fluid buoyancy).

Figure 5A:
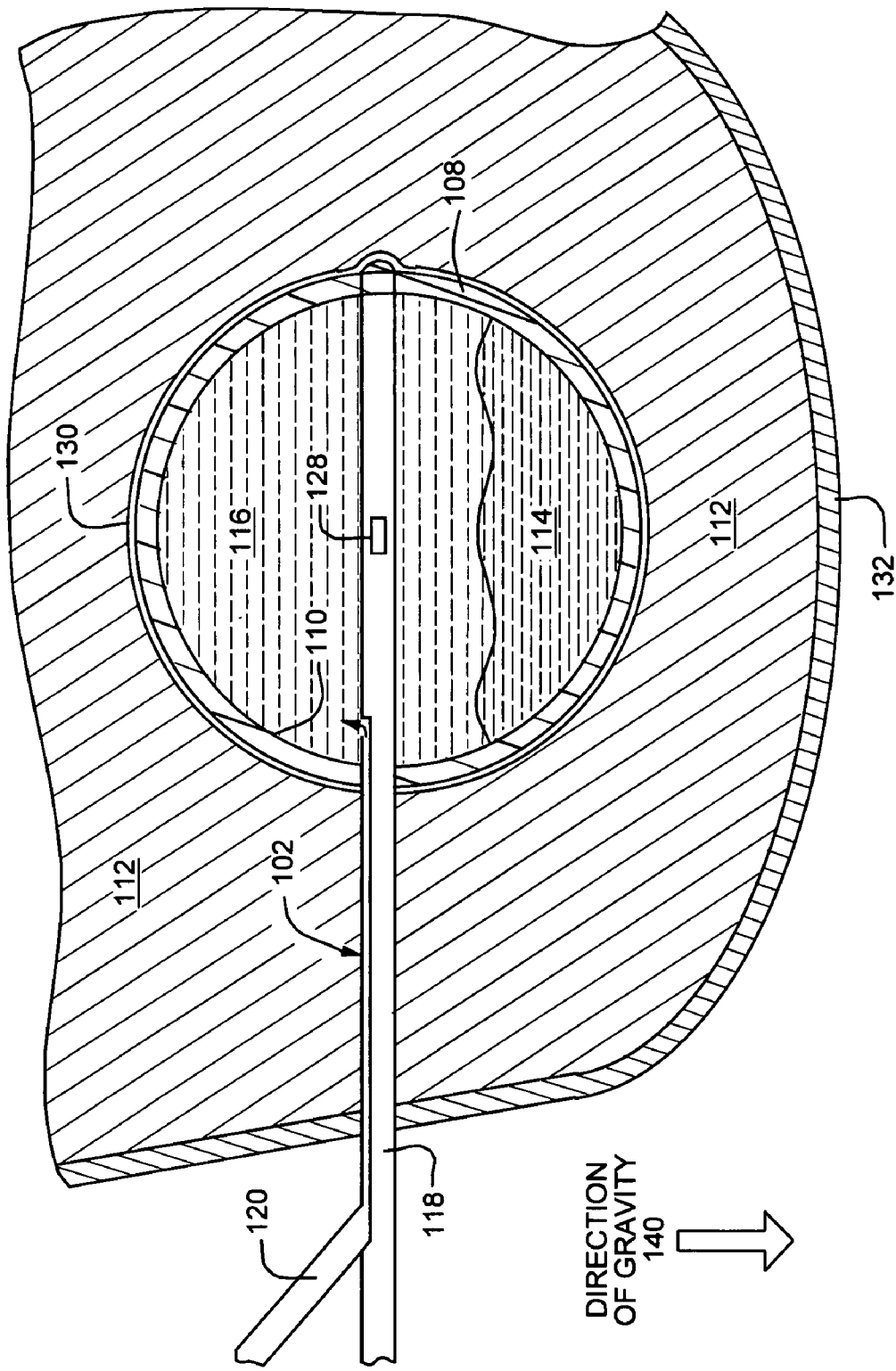
FIG. 5A illustrates a cross-sectional view of an exemplary brachytherapy treatment device having fluid therein which is oriented with relation to direction of gravity.
Figure 5B:
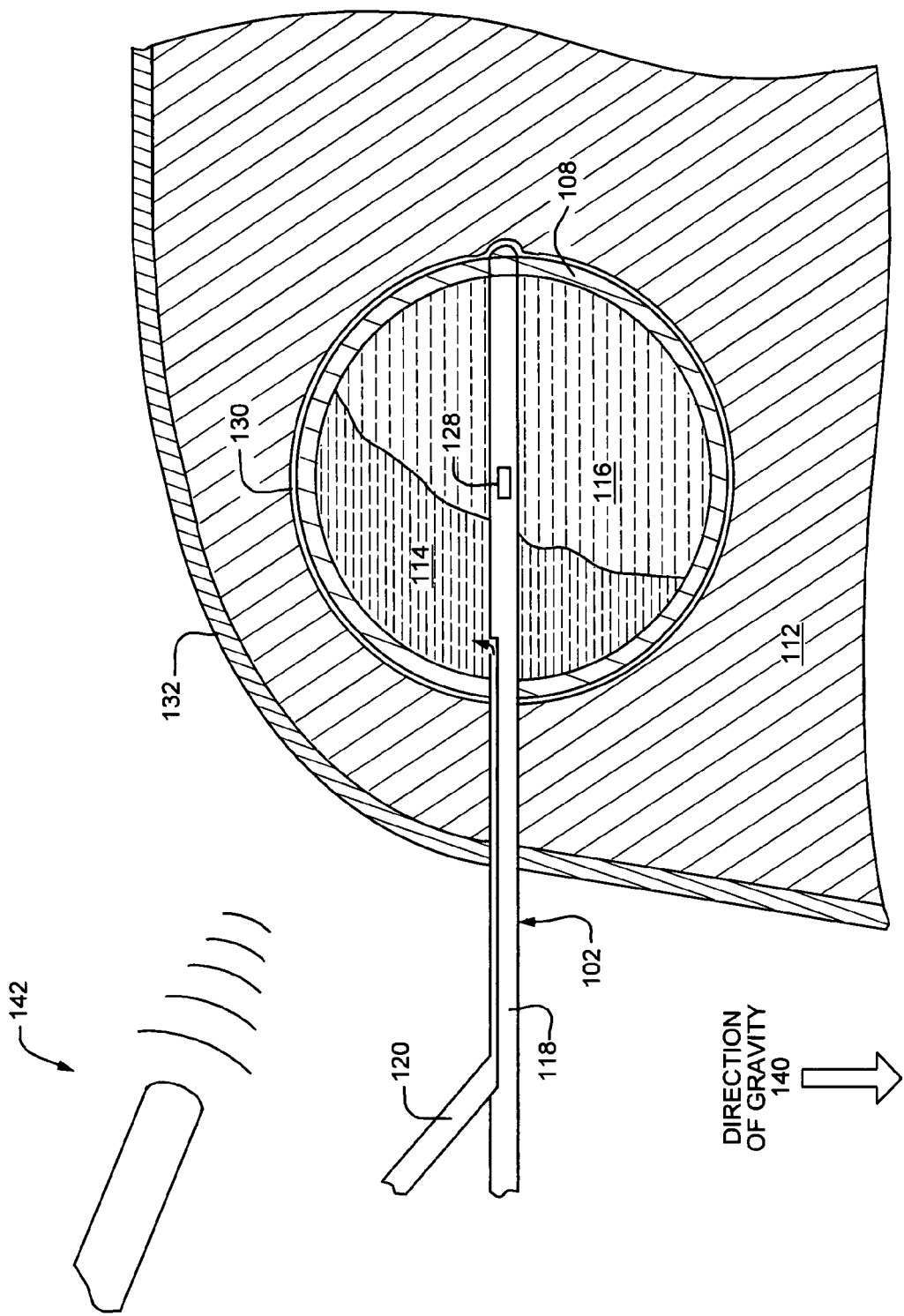
FIG. 5B illustrates a cross-sectional view of an exemplary brachytherapy treatment device having fluid therein which is oriented with relation to an external stimuli.

FIGS. 5A and 5B illustrate various orientations for fluid radiation shield formed by first and second immiscible fluids 114, 116. At least first and second immiscible fluids 114, 116 may be disposed within expandable chamber 108 via inflation lumen 120. The first and second immiscible fluids 114, 116 may be injected into the expandable chamber 108 in a number of different ways and may enter expandable chamber 108 via any number of different port paths or apertures (shown generally as arrows in FIGS. 5A & 5B). As shown in FIGS. 5A & 5B, both the first and second immiscible fluids 114, 116 may be inserted via the same inflation lumen 120. To enhance the ability to independently orient the first and second immiscible fluids 114, 116, they should not be capable of mixing or homogenizing. In some implementations it may be desirable to use only one radiation shielding fluid, while in other implementations it may be desirable to use two, three, or more immiscible fluids.

With reference now to FIG. 5A, the direction of gravity is shown by arrow 140. Based on the direction of gravity 140 and the position of the first and second immiscible fluids 114, 116, the first immiscible fluid 114 would have a higher density than that of second immiscible fluid 116. Based upon the relative locations of the radiation source position 128 and the skin 132, it would be desirable for first immiscible fluid 114 to function as a radiation shielding fluid, thus first immiscible fluid 114 would have a higher radiation absorption property than that of second immiscible fluid 116. In some embodiments, as shown in FIG. 5A, a treatment site (i.e., a patient) may be oriented with relation to the direction of gravity to orient the first and second shielding fluids 114, 116 appropriately.

In some instances it may be difficult or uncomfortable to orient a treatment site (i.e. patient) properly with relation to the direction of gravity and thus it may be desirable to use other methods of orienting the first and second immiscible fluids 114, 116 within the expandable chamber 108. As shown in FIG. 5B, the first and second immiscible fluids 114, 116 may be oriented by a stimuli 142 instead of by the direction of gravity 140. Stimuli 142 is shown as external (to skin 132) for exemplary purposes of illustration, but stimuli 142 may also applied internally, such as via insertion member 102. An external stimuli may be applied by a machine or by a user (e.g., physician) at an appropriate location external to skin 132 to orient first immiscible fluid 114 into position, such as shown in FIG. 5B.

The first and second immiscible fluids 114, 116 may orient with relation to the external stimuli 142. The external stimuli 142 may be anything which can affect the orientation of the first and second immiscible fluids 114, 116, such as a magnet, cooling element, heating element, just to name a few examples. In these exemplary embodiments, the first and second immiscible fluids 114, 116 may have yet additional properties to allow them to orient with relation to the external stimuli 142, such as metallic properties, shape memory properties, or other temperature- or state-dependent change properties. As shown in FIG. 5B, the first immiscible fluid 114 would provide fluid shielding of skin 132, and thus would have a higher radiation absorption property than that of second immiscible fluid 116 to shield skin 132.

Figure 6:
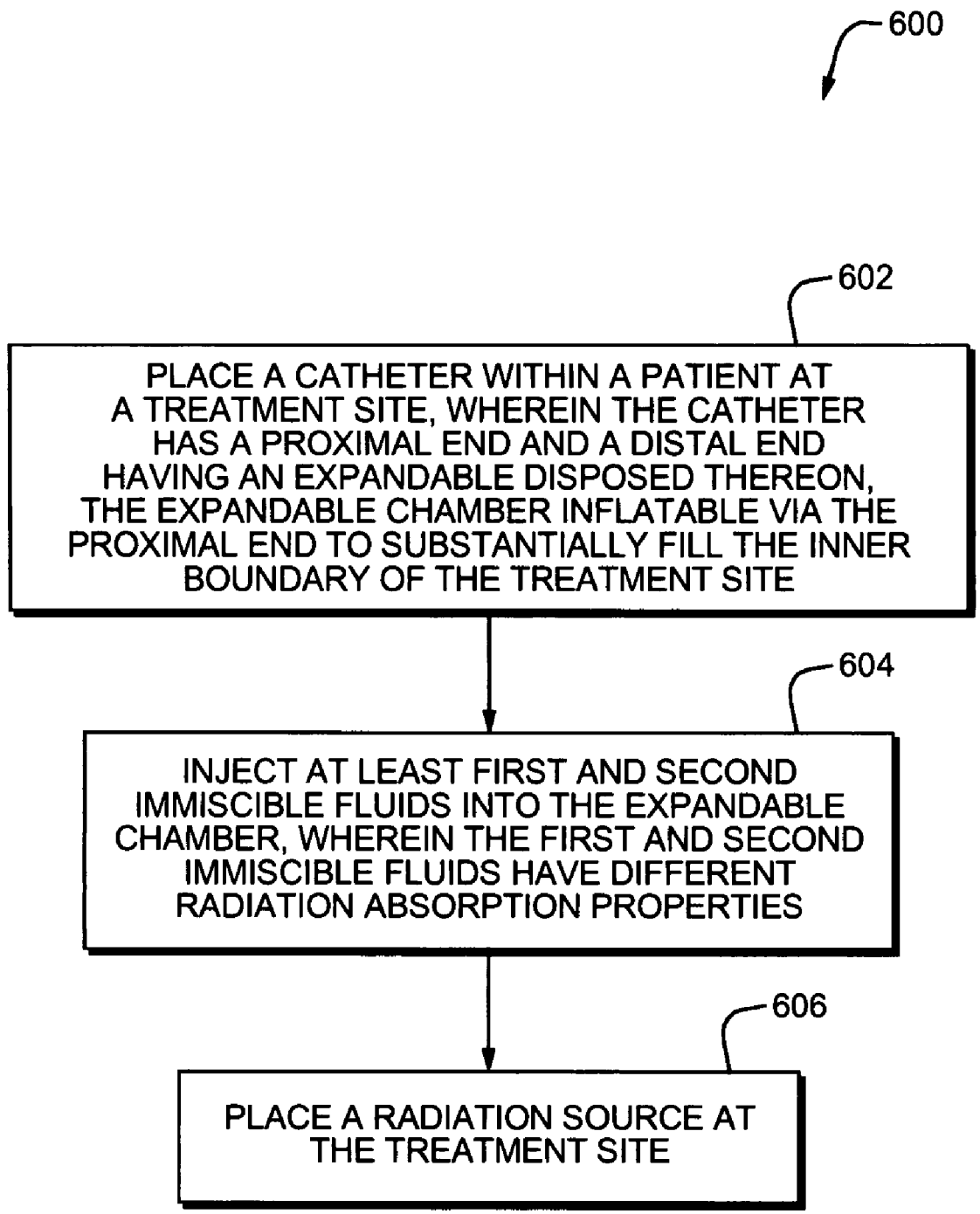
FIG. 6 is a flow diagram illustrating an exemplary method for performing brachytherapy treatment.

Methods for delivering brachytherapy treatment to a treatment site in a patient are also provided herein. One exemplary method 600 of performing brachytherapy treatment is shown generally in FIG. 6. The method may commence with the placement 602 of a catheter within a patient at a treatment site. The catheter may comprise a tubular insertion member 102, as previously described above. Prior to placement 602 of the catheter, it is common for a surgery to have been performed to remove as much of a tumor as possible. A surgical resection of the tumor is typically performed, leaving a surgical pathway and a resected space or cavity for placement of the catheter within the patient. In some embodiments, the placement of the catheter may include surgically resection, incising, or otherwise altering a patient's tissue.

Once the catheter is appropriately positioned within a patient, one or more expandable chambers 108, 109 may be inflated, for example, to fill the cavity of a resected tumor. The tissue surrounding the cavity may substantially conform to the outer surface of the outer expandable chamber (108 or 109). In this manner, the tissue surrounding the cavity 130 may also be positioned to reshape tissue to reshape the radiation dose profile and this may be utilized in conjunction with a desired fluid radiation shield orientation to achieve a predetermined radiation dosing profile.

The method may continue by injecting 604 at least first and second immiscible fluids into the expandable chamber. The first and second immiscible fluids have different radiation absorption properties and other distinguishing properties allowing them to orient within the expandable chamber in a predetermined orientation. The method then includes placing 606 a radiation source at the treatment site. When the radiation source is placed the dose profile is reshaped by the fluid shield formed by at least one of the first and second immiscible fluids. Following radiation treatment, the catheter may remain within the patient's body in the treatment position so that it can be used during the next treatment session, or it may be removed.

In another embodiment, when the first and second immiscible fluids may orient using direction of gravity and fluid buoyancy to for a predetermined orientation, the method may further include positioning a patient. If the first and second immiscible fluids utilize gravity and fluid buoyancy to properly orient then it will be important to position the treatment site (i.e., patient) properly with relation the direction of gravity. In yet another embodiment, the patient may be positioned to allow a stimuli to orient at least one of the first and second fluids within the expandable chamber.

In other embodiments, the method may further comprise applying a stimuli to stimulate placement of the first and second immiscible fluids into a predetermined orientation. The method may commence by injecting a first immiscible fluid into the expandable chamber. The stimuli may then be applied to cause the first immiscible fluid in the expandable chamber to undergo a change, before injecting the second immiscible fluid into the expandable chamber. This may be advantageous, for example, where it is desirable to inject and then 'gel' a first immiscible fluid into place before filling the remainder of the cavity with a second immiscible fluid.

Disclosed herein are devices and methods for use in treating proliferative tissue disorders by the application of radiation, energy, or other therapeutic rays. While the devices and methods disclosed herein are particularly useful in treating various cancers and luminal strictures, a person skilled in the art will appreciate that the methods and devices disclosed herein can have a variety of configurations, and they can be adapted for use in a variety of medical procedures requiring treatment using sources of radioactive or other therapeutic energy. These sources can be radiation sources such as radioisotopes, or man-made radiation sources such as x-ray generators. The source of therapeutic energy can also include sources of thermal, radio frequency, ultrasonic, electromagnetic, and other types of energy.

It should be understood that various changes and modifications to the above-described embodiments will be apparent to those skilled in the art. The examples given herein are not meant to be limiting, but rather are exemplary of the modifications that can be made without departing from the spirit and scope of the described embodiments and without diminishing its attendant advantages.

What is claimed is:

1. A brachytherapy treatment device, comprising:
   a tubular insertion member having a proximal end and a distal end;
   an expandable chamber disposed on the distal end of the tubular insertion member and having an inner surface defining a three-dimensional volume; and
   first and second immiscible fluids disposed within the expandable chamber and having different radiation absorption properties, wherein at least one of the first and second immiscible fluids forms a fluid radiation shield having a predetermined orientation within the three-dimensional volume.

2. The device of claim 1, wherein the first and second immiscible fluids have different densities and utilize fluid buoyancy to form a fluid radiation shield having a predetermined orientation.

3. The device of claim 1, wherein the first and second immiscible fluids form an asymmetric fluid radiation shield to create an asymmetric radiation dosing profile relative to an inner boundary of target tissue.

4. The device of claim 1, wherein the predetermined orientation of the fluid radiation shield is determined by direction of gravity.

5. The device of claim 1, wherein the predetermined orientation of the fluid radiation shield is determined by application of an external stimuli.

6. The device of claim 1, wherein the at least one of the first and second immiscible fluids disposed within the expandable chamber forms a solid radiation shield having a predetermined orientation.

7. The device of claim 1, further comprising a second expandable chamber disposed on the distal end of the tubular insertion member, the second expandable chamber surrounding the expandable chamber.

8. The device of claim 1, further comprising a radiation source position located within the expandable chamber, wherein the and second immiscible fluids substantially surround the radiation source position.

9. A method for performing brachytherapy treatment, comprising:
    placing a catheter within a patient at a treatment site, wherein the catheter has a proximal end and a distal end having an expandable chamber disposed thereon, the expandable chamber inflatable via the proximal end to substantially fill an inner boundary of the treatment site;
    injecting at least first and second immiscible fluids into the expandable chamber, wherein the first and second immiscible fluids have different radiation absorption properties; and
    placing a radiation source at the treatment site.

10. The method of claim 9, wherein orientation of the first and second immiscible fluids relative to the radiation source forms a predetermined fluid radiation shield.

11. The method of claim 9, wherein the first and second immiscible fluids have different densities and utilize fluid buoyancy to create an asymmetric fluid radiation shield.

12. The method of claim 9, wherein the first and second immiscible fluids form a predetermined fluid radiation shield to create an asymmetric radiation dosing profile relative to an inner boundary of the treatment site.

13. The method of claim 9, further comprising positioning the patient to allow a stimuli to orient at least one of the first and second immiscible fluids within the expandable chamber.

14. The method of claim 9, further comprising applying a stimuli to change a physical state of at least one of the first and second immiscible fluids.

15. The method claim 9, wherein the predetermined orientation of the fluid radiation shield is determined by direction of gravity.

16. The method claim 9, wherein the predetermined orientation of the fluid radiation shield is determined by external stimuli.

17. The method of claim 9, further comprising the steps of:
    injecting the first immiscible fluid into the expandable chamber;
    applying a stimuli to cause the first immiscible fluid in the expandable chamber to change physical state; and
    injecting the second immiscible fluid into the expandable chamber.

* * * * *